United States Patent [19]

Wroblowsky et al.

[11] Patent Number: 5,594,148

[45] Date of Patent: Jan. 14, 1997

[54] PROCESS FOR THE PREPARATION OF ALKOXYTRIAZOLINONES

[75] Inventors: Heinz-Jürgen Wroblowsky, Langenfeld; Klaus König, Odenthal, both of Germany

[73] Assignee: Bayer Aktiengesellschaft, Leverkusen, Germany

[21] Appl. No.: 529,185

[22] Filed: Sep. 15, 1995

[30] Foreign Application Priority Data

Sep. 23, 1994 [DE] Germany ............... 44 33 969.0

[51] Int. Cl.$^6$ ................................. C07D 249/12
[52] U.S. Cl. ............................................ 548/263.6
[58] Field of Search ............................. 548/263.6

[56] References Cited

U.S. PATENT DOCUMENTS 5,356,865  10/1994  Muller et al. .
5,488,028   1/1996  Haas et al. .

FOREIGN PATENT DOCUMENTS 0507171  10/1992  European Pat. Off. .

OTHER PUBLICATIONS

Chem. Abstracts 82:86060x (1975).
Chem. Abstracts vol. 42: 8109d (1948).
J. Indian Chem. Soc. vol. 6 (1929) pp. 565–575 (In English).
J. Chem. Soc. Perkin I 1973, pp. 2644–2646 (in English).

*Primary Examiner*—Patricia L. Morris
*Attorney, Agent, or Firm*—Sprung Horn Kramer & Woods

[57] ABSTRACT

Alkoxytriazolinones of the general formula (I), in which $R^1$ and $R^2$ independently of one another represent in each case optionally substituted alkyl, alkenyl, alkinyl, cycloalkyl, cycloalkylalkyl, aryl or arylalkyl, (which can be used as intermediates for the preparation of herbicidal active compounds) are obtained in very good yields and in high purity by reacting iminocarbonic diesters (II) with carbazinic esters (III)

in which $R^3$ and $R^4$ in each case represent, for example, alkyl or aryl, at –20° C. to +120° C. (1st step) and subjecting the semicarbazide derivatives (IV) formed in this process with elimination of $R^3$-OH to a cyclizing condensation reaction in the presence of a base at +20° C. to 100° C. with elimination of $R^4$-OH, if appropriate after intermediate isolation (2nd step).

13 Claims, No Drawings

PROCESS FOR THE PREPARATION OF ALKOXYTRIAZOLINONES

The invention relates to a new process for the preparation of alkoxytriazolinones, most of which are known and which can be used as intermediates for the preparation of agrochemical active compounds, it also being possible for the process to be carried out on an industrial scale.

Alkoxytriazolinones and a plurality of methods for their preparation are already known (cf. J. Indian Chem. Soc. 6 (1929), 565–575; J. Chem. Soc. Perkin I 1973, 2644–2646; Arch. Pharm. 307 (1974), 889–891; EP-A 477646; EP-A 507171). However, these known synthetic methods give alkoxytriazolinones only in highly unsatisfactory yields.

It is furthermore known to form 5-methoxy-4-methyl-2, 4-dihydro-3H-1,2,4-triazol-3-one by methylating urazole or 4-methylurazole with diazomethane ($CH_2N_2$) [cf. F. Arndt et al, Rev. Fac. Sci. Istanbul 13A, pp. 127 to 144 (1948)]; while this method affords high yields of the triazolinone, it cannot be carried out on an industrial scale.

It has now been found that alkoxytriazolinones of the general formula (I)

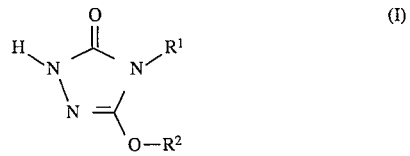

in which
$R^1$ represents in each ease optionally substituted alkyl, alkenyl, alkinyl, cycloalkyl, cycloalkylalkyl, aryl or arylalkyl and
$R^2$ represents in each case optionally substituted alkyl, alkenyl, alkinyl, cycloalkyl, cycloalkylalkyl, aryl or arylalkyl,
are obtained in very good yields and in high purity when iminocarbonic diesters of the general formula (II)

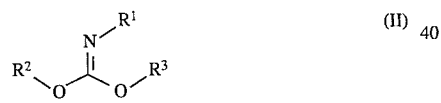

in which
$R^1$ and $R^2$ have the abovementioned meanings and
$R^3$ represents in each case optionally substituted alkyl, aryl or arylalkyl,
are reacted with carbazinic esters of the general formula (III)

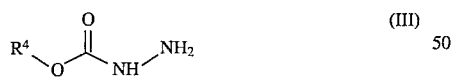

in which
$R^4$ represents in each case optionally substituted alkyl, aryl or arylalkyl,
if appropriate in the presence of a reaction auxiliary and if appropriate in the presence of a diluent at temperatures between −20° C. and +120° C. ("first reaction step") and the semicarbazide derivatives formed in this process of the general formula (IV)

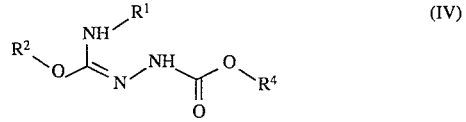

in which
$R^1$, $R^2$ and $R^4$ have the abovementioned meanings,
and/or the corresponding tautomeric compounds are subjected to a cyclizing condensation reaction, at temperatures between 20° C. and 100° C., if appropriate after intermediate isolation, in the presence of a base and if appropriate in the presence of a diluent ("second reaction step").

Surprisingly, the alkoxytriazolinones of the general formula (I) can be obtained in considerably higher yields by the process according to the invention than by most of the known synthetic methods.

Compared with the "diazomethane method" (F. Arndt et al, 1. c.) the decisive advantage of the process according to the invention is that it can also be carried out on an industrial scale.

In contrast to the known process, which is to be carried out at higher temperatures and in which phenol is formed as coupling product—$R^4$ represents phenyl (cf. EP-A 507171, Examples II-1 and II-2)—the process according to the invention can also be carried out in a problem-free manner with the elimination of simple alkanols, which can be recovered in a much simpler fashion and requiring less energy than in the case of phenol.

In contrast to the prior art (cf. EP-A 507171), it is also possible in many cases advantageously to employ "asymmetric" iminocarbonic diesters (in which case $R^2$ and $R^3$ have a different meaning, $OR^3$ being a better leaving group than $OR^2$) as starting substances. Very good components $R^3$ in the leaving groups $OR^3$ which may be mentioned are, for example, methyl, ethyl, phenyl, benzyl, methoxyethyl and ethoxyethyl.

The process according to the invention therefore represents a valuable enrichment of the prior art.

The invention preferably relates to the preparation of compounds of the formula (I) in which
$R^1$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, and
$R^2$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

The invention particularly relates to the preparation of compounds of the -formula (I) in which
$R^1$ represents methyl, ethyl, n- or i- propyl or n-, i-, s- or t-butyl, each of which is optionally substituted by fluorine, chlorine and/or bromine, methoxy or ethoxy, or represents propenyl, butenyl, propinyl or butinyl, each of which is optionally substituted by fluorine, chlorine and/ or bromine, or represents cyclopropyl, cyclobutyl or cyclopropylmethyl, each of which is optionally substituted by fluorine, chlorine, bromine, methyl or ethyl, or represents phenyl or benzyl, each of which is optionally substituted by carboxyl, cyano, fluorine, chlorine, bromine, methyl, ethyl, trifluoromethyl, methoxy, ethoxy, difluoromethoxy, trifluoromethoxy, methoxycarbonyl or ethoxycarbonyl, and $R^2$ represents methyl, ethyl, n- or i- propyl or n-, i-, s- or t-butyl, each of which is optionally substituted by fluorine, chlorine and/or bromine, methoxy or ethoxy, or represents propenyl, butenyl, propinyl or butinyl, each of which is optionally substituted by fluorine, chlorine and/or bromine, or represents cyclopropyl, cyclobutyl or cyclopropylmethyl, each of which is optionally substituted by fluorine, chlorine, bromine, methyl or ethyl, or represents phenyl or benzyl, each of which is optionally substituted by carboxyl, cyano, fluorine, chlorine, bromine, methyl, ethyl, trifluoromethyl, methoxy, ethoxy, difluoromethoxy, trifluoromethoxy, methoxycarbonyl or ethoxycarbonyl.

If, for example, O-(2-ethoxy-ethyl) O-n-propyl methyliminocarbonate and ethyl carbazinate are used as starting substances, the course of the reaction-in the process according to the invention can be outlined by the following equation:

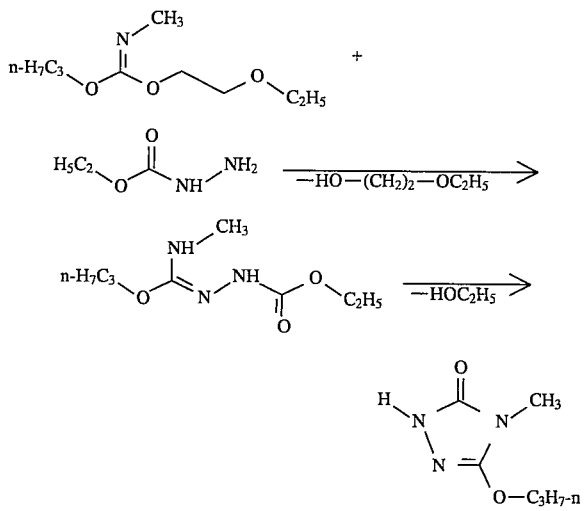

Formula (II) provides a general definition of the iminocarbonic diesters to be used as starting substances in the process according to the invention for the preparation of the compounds of the general formula (I). In formula (II), $R^1$ and $R^2$ preferably, or in particular, have those meanings which have already been mentioned above in connection with the description of the compounds of the formula (I) as preferred, or as particularly preferred, for $R^1$ and $R^2$; $R^3$ preferably represents $C_1$–$C_4$-alkyl, phenyl or benzyl, each of which is optionally substituted by $C_1$–$C_4$-alkoxy, phenoxy or benzyloxy, and in particular represents methyl, ethyl, propyl, cyclopropyl, methoxyethyl or ethoxyethyl.

The starting substances of the formula (II) are known and/or can be prepared by processes known per se (cf. Chem. Ber. 120 (1987), 339–344; preparation examples).

Formula (III) provides a general definition of the carbazinic esters furthermore to be used as starting substances in the process according to the invention. In formula (III), $R^4$ preferably represents $C_1$–$C_4$-alkyl, phenyl or benzyl, each of which is optionally substituted by $C_1$–$C_4$-alkoxy, phenoxy or benzyloxy, and in particular represents methyl, ethyl, propyl, methoxyethyl or ethoxyethyl.

The starting substances of the formula (III) are known chemicals for organic synthesis.

Diluents which are suitable for carrying out the process according to the invention are (for both reaction steps) the customary organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methyl-pyrrolidone or hexamethylphosphoric triamide; esters such as methyl acetate or ethyl acetate; sulphoxides such as dimethyl sulphoxide; alcohols such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether: mixtures of these with water, or pure water.

Alcohols such as methanol, ethanol or n- or i-propanol are particularly preferred as diluents.

If appropriate, however, it is also possible for the reactions according to the invention to be carried out without the use of diluents.

The first step of the process according to the invention is preferably carried out in the presence of a suitable reaction auxiliary. Suitable reaction auxiliaries are preferably protonic acids such as, for example, hydrochloric acid, sulphuric acid, phosphoric acid, carbonic acid, acetic acid, propionic acid, pivalic acid, methanesulphonic acid, benzoic acid, benzenesulphonic acid and p-toluenesulphonic acid, if appropriate also polymeric acids or acidic ion exchangers.

Particularly preferred reaction auxiliaries in the first step of the process according to the invention are pivalic acid, acetic acid and (aqueous) hydrochloric acid.

The second step of the process according to the invention is carried out in the presence of a base. Suitable bases are all the conventional inorganic or organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also basic organic nitrogen compounds such as trimethylamine, triethylamine, tributylamine, N,N-dimethylaniline, N,N-dimethyl-benzylamine, pyridine, N-methylpiperidine, N,N-dimethylaminopyridine, 5-ethyl-2-methylpyridine, diazabicyclooctane (DABCO), diazabicyclononene (DBN) or diazabicycloundecene (DBU).

Particularly preferred as bases in the second step of the process according to the invention are alkali metal alcoholates such as sodium methylate or sodium ethylate, and alkali metal hydroxides such as sodium hydroxide or potassium hydroxide, in each case dissolved, if appropriate, in an appropriate alcohol or in water.

When carrying out the first step of the process according to the invention, the reaction temperatures can be varied within a substantial range. In general, the process is carried out at temperatures between –20° C. and 120° C., preferably at temperatures between 0° C. and 100° C., in particular at temperatures between 20° C. and 80° C.

When carrying out the second step of the process according to the invention, the reaction temperatures can be varied within a substantial range. In general, the process is carried out at temperatures between 20° C. and 100° C., preferably at temperatures between 30° C. and 90° C., in particular at temperatures between 40° C. and 80° C.

Both steps of the process according to the invention are generally carried out under atmospheric pressure. However, it is also possible to carry out the process under elevated or reduced pressure, in general between 0.1 bar and 10 bar.

For carrying out the process according to the invention for the preparation of the compounds of the formula (I), 0.5 to 1.2 mol, preferably 0.8 to 1.1 mol, of carbazinic ester of the formula (III) and, if appropriate, 0.001 to 2.0 mol, preferably 0.01 to 1.0 mol, of reaction auxiliary are generally employed per mole of iminocarbonic diester of the formula (II).

In a preferred embodiment of the process according to the invention, the starting substances of the formula (II) and of the formula (III) and, if appropriate, a reaction auxiliary are mixed in a suitable diluent and stirred at the temperature required until virtually no starting material is present. The intermediate of the formula (IV) can then be isolated in the customary manner, for example by concentrating the mixture, digesting the residue with an organic solvent, such as, for example, methyl t-butyl ether, and filtering with suction. Alternatively, the intermediate of the formula (IV) can be treated with a base—if appropriate dissolved in one of the abovementioned diluents—and the mixture stirred at the temperature required for cyclizing condensation until the reaction has ended, without intermediate isolation.

Working-up to isolate the products of the formula (I) can be effected by customary methods. For example, the mixture is concentrated, the product is taken up in water, and the mixture is neutralized or acidified, for example using hydrochloric acid. If the product is obtained as crystals in this process, it is isolated by filtration with suction. If not, it is shaken with an organic solvent which is virtually immiscible with water, such as, for example, ethyl acetate, and the organic phase is dried—for example using magnesium sulphate—and filtered. After the solvent has been removed carefully by distillation under reduced pressure, the product of the formula (I) is then obtained as a residue.

The resulting crude products can be purified by recrystallization, stirring with a suitable organic solvent, such as, for example, petroleum ether, or by distillation.

The compounds of the formula (I) to be prepared by the process according to the invention can be used as intermediates for the preparation of herbicidally active compounds (cf. EP-A 477646 and EP-A 507171).

PREPARATION EXAMPLES

EXAMPLE 1

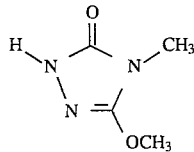

A mixture of 208 g (2.0 mol) of ethyl carbazinate, 206 g (2.0 mol) of dimethyl methyliminocarbonate and 500 ml of methanol is stirred for 12 hours at 50° C. and for a further 3 hours at 70° C. 360 g of a 30% strength solution of sodium methanolate in methanol (2.0 mol of NaOCH$_3$) are then added at 40° C., and the reaction mixture is stirred for 3 hours at 50° C. The mixture is then neutralized using 20% strength aqueous hydrochloric acid, with ice-cooling, and most of the methanol is subsequently distilled off while the remainder is made up to approximately 500 ml with water. After the mixture has been left to stand for several hours at 5° C., the crude product which is obtained as crystals (243 g) is isolated by filtration with suction. Besides 6.7% of water, it still contains small amounts of sodium chloride and organic impurities. For purification, it is taken up in 750 ml of toluene, freed from water by azeotropic distillation and filtered while hot. The filtrate is cooled and the crystalline product isolated by filtration with suction.

207 g (80% of theory) of 5-methoxy-4-methyl-2,4-dihydro-3H-1,2,4-triazol-3-one of melting point 148° C. are obtained.

EXAMPLE 2

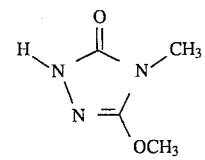

A mixture of 208 g (2.0 mol) of ethyl carbazinate, 206 g (2.0 mol) of dimethyl methyliminocarbonate, 4.0 g (0.04 mol) of pivalic acid and 1250 ml of methanol is stirred for 3 days at 20° C. 360 g of a 30% strength solution of sodium methanolate in methanol (2.0 mol of NaOCH$_3$) are then added at 40° C., and the reaction mixture is stirred for 3 hours at 50° C. It is subsequently neutralized using strength hydrochloric acid and worked up further as described in Example 1.

220 g (85% of theory) of 5-methoxy-4-methyl-2,4-dihydro-3H-1,2,4-triazol-3-one of melting point 148° C. are obtained.

EXAMPLE 3

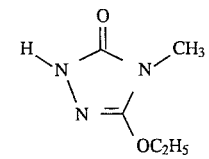

A mixture of 1740 g (16.56 mol) of ethyl carbazinate, 2169 g (16.56 mol) of diethyl methyliminocarbonate and 2 liters of ethanol is stirred for 16 hours at 50° C. and for a further 8 hours at 80° C. 2982 g of a 30% strength solution of sodium methanolate in methanol (16.56 mol of NaOCH$_3$) are then added dropwise at 50° C., and the reaction mixture is stirred for 3 hours at 50° C. The mixture is then neutralized using 30% strength aqueous hydrochloric acid, with ice cooling, and subsequently concentrated under reduced pressure. The residue is taken up in 2.5 liters of N,N-dimethylformamide which has been heated to 80° C., and the mixture is freed from sodium chloride by filtration with suction. The filtrate is concentrated, and the crude product obtained as residue is purified by distillation in vacuo and, after it has solidified, recrystallized from toluene.

2019 g (89% of theory) of 5-ethoxy-4-methyl-2,4-dihydro-3H-1,2,4-triazol-3-one of melting point 126° C. are obtained.

EXAMPLE 4

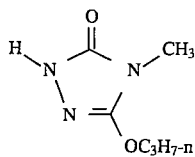

A solution of 612 g (6.0 mol) of pivalic acid in 200 ml of n-propanol is added dropwise at 0° C. to a mixture of 630 g (6.0 mol) of ethyl carbazinate, 954 g (6.0 mol) of dipropyl methyliminocarbonate and 600 ml of n-propanol, while cooling with an ice/sodium chloride mixture, and the complete mixture is stirred for 30 minutes at 0° C. to 10° C. 2169 g of a 30% strength solution of sodium methanolate in methanol (12 mol of $NaOCH_3$) are then added, and the reaction mixture is stirred for 3 hours at 50° C. The mixture is then neutralized using concentrated hydrochloric acid, with ice-cooling, and subsequently freed from sodium chloride by filtration with suction, and the filtrate is concentrated. The crude product obtained as residue is purified by distillation in vacuo.

808 g (83% of theory) of 4-methyl-5-propoxy-2,4-dihydro-3H-1,2,4-triazol-3-one are obtained as a waxy product. Melting point: 74° C. (from acetone).

EXAMPLE 5

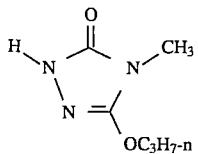

A solution of 20.4 g (0.2 mol) of pivalic acid in 10 ml of n-propanol is added dropwise with ice-cooling to a mixture of 104 g (1.0 mol) of ethyl carbazinate, 159 g (1.0 mol) of dipropyl methyliminocarbonate and 200 ml of n-propanol, and the complete mixture is stirred for 30 minutes without cooling. 108 g of a 30% strength solution of sodium methanolate in methanol (0.6 mol of $NaOCH_3$) are then added, and the reaction mixture is stirred for 3 hours at 50° C. and for a further 4 hours at 60° C. to 80° C. The mixture is then neutralized using concentrated hydrochloric acid, with ice-cooling, and subsequently concentrated under reduced pressure. The crude product which remains in the residue is purified by distillation in vacuo.

137 g (82.5% of theory) of 4-methyl-5-propoxy-2,4-dihydro-3H-1,2,4-triazol-3-one are obtained as a waxy product. Melting point: 74° C. (from acetone).

EXAMPLE 6

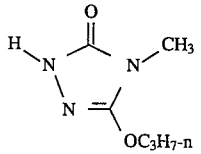

25 g (123 mmol) of ethyl N'-(α-methylamino-α-propoxymethylene)-hydrazine-N-carboxylate are introduced into 200 ml of methanol, and 23.2 g of a solution of sodium methanolate (127 mmol of $NaOCH_3$) in methanol are added dropwise at 5° C. to 10° C. The mixture is stirred for 6 hours at 50° C. and then concentrated under a water pump vacuum. The residue is taken up in 100 ml of water and acidified using concentrated hydrochloric acid, with ice-cooling. After the solution has been saturated with sodium chloride, it is extracted five times using ethyl acetate. The combined extraction solutions are dried using magnesium sulphate and filtered. The solvent is carefully removed from the filtrate by distillation under reduced pressure. 17.75 g (88.5% of theory) of 4-methyl-5-propoxy-2,4-dihydro-3H-1,2,4-triazol-3-one are obtained as a waxy product. Melting point: 74° C. (from acetone).

EXAMPLE 7

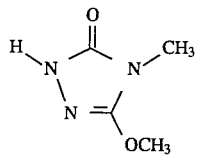

14 g (80 mmol) of ethyl N'-(α-methylamino-α-methoxymethylene)-hydrazine-N-carboxylate are introduced into 120 ml of methanol, and 7.6 g of a solution of sodium hydroxide (86 mmol of NaOH) in water are then added dropwise. The mixture is stirred for 5 hours at 50° C. and then concentrated under a water pump vacuum. The residue is acidified using 20% strength aqueous hydrochloric acid and the product obtained as crystals is isolated by filtration with suction.

11.3 g of 5-methoxy-4-methyl-2,4-dihydro-3H-1,2,4-triazol-3-one (73% pure, remainder: sodium chloride) are obtained; yield: 80% of theory.

EXAMPLE 8

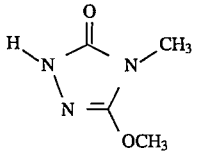

14 g (80 mmol) of ethyl N'-(α-methylamino-α-methoxymethylene)-hydrazine-N-carboxylate are introduced into 120 ml of methanol, and 15.2 g of a solution of sodium methanolate (84 mmol of $NaOCH_3$) in methanol are added dropwise at 10° C. The mixture is stirred for 6 hours at 50° C. and then concentrated under a water pump vacuum. The residue is taken up in 50 ml of a saturated aqueous sodium chloride solution and acidified using 12% strength hydrochloric acid, with ice-cooling. The product obtained as crystals is isolated by filtration with suction.

11.2 g of 5-methoxy-4-methyl-2,4-dihydro-3H-1,2,4-triazol-3-one (91% pure, remainder: sodium chloride) are obtained; yield: 99% of theory.

EXAMPLE 9

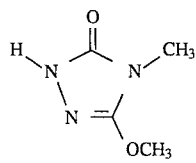

83.8 g (0.794 mol) of ethyl carbazinate are introduced into 500 ml of methanol, 88 g (0.833 mol) of dimethyl methyliminocarbonate are then added dropwise, and 0.95 g (0.016 mol) of acetic acid are added. The mixture is stirred for 15 hours and, after a further 4.2 g (0.04 mol) of dimethyl methyliminocarbonate and 0.48 g (0.008 mol) of acetic acid have been added, for a further 6 hours at 20° C. 74.7 g of 45% strength aqueous sodium hydroxide solution (0.84 mol of NaOH) are then run in, and the mixture is heated for 6 hours at 55° C. to 58° C. The solvent is subsequently removed under a water pump vacuum, the residue is taken up in 220 ml of ice-water, and the pH is brought to approximately 6 by adding concentrated hydrochloric acid, with ice-cooling. The product obtained as crystals is isolated by filtration with suction.

104 g (85% of theory) of 5-methoxy-4-methyl-2,4-dihydro-3H-1,2,4-triazol-3-one (86.8% pure, remainder: sodium chloride and water) are obtained.

EXAMPLE 10

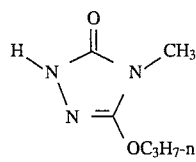

A mixture of 147.4 g (1.4 mol) of ethyl carbazinate, 265 g (1.4 mol) of O-(2ethoxyethyl) O-n-propyl methyliminocarbonate and 150 ml of propanol is heated for 10 hours at 80° C. and for a further 2 hours at 100° C. After the mixture has cooled to 50° C., 252 g of a 30% strength solution of sodium methanolate in methanol (1.4 mol of NaOCH₃) are metered in in the course of 30 minutes. After the mixture has been stirred for 3 hours at 50° C., it is neutralized by adding 138 g of concentrated hydrochloric acid (1.4 mol of HCl), while cooling with ice/sodium chloride. Methanol, propanol, ethoxyethanol and water are then distilled off to a substantial extent under a water pump vacuum at a bottom temperature of 80° C. The crude product which remains as residue is isolated by distillation in vacuo over a bridge-shaped stillhead which has been heated to 80° C.

208 g of 4-methyl-5-propoxy-2,4-dihydro-3H-1,2,4-triazol-3-one (90.1% pure, yield: 85.5% of theory) are obtained, and this can be obtained in pure form by recrystallization from toluene/cyclohexane (1:1). Melting point: 74° C.

EXAMPLE 11

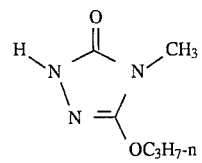

3.6 g of pivalic acid are added with ice-cooling to a mixture of 147.4 g (1.4 mol) of ethyl carbazinate, 265 g (1.4 mol) of O-(2-ethoxyethyl) O-n-propyl methyliminocarbonate and 200 ml of propanol, and the mixture is stirred for one hour at 20° C. A further 3.6 g of pivalic acid are then added, and the stirrer is switched off. After a further 2 hours at 20° C., the batch has crystallized fully. A homogeneous mixture is obtained again by heating the batch to 50° C. 252 g of a 30% strength solution of sodium methanolate in methanol (1.4 mol of NaOCH3) are then metered in in the course of 30 minutes. After the mixture has been stirred for 3 hours at 50° C., it is neutralized by adding 138 g of concentrated hydrochloric acid (1.4 mol of HCl), while cooling with ice/sodium chloride. Methanol, propanol, ethoxyethanol and water are then distilled off to a substantial extent under a water pump vacuum at a bottom temperature of 80° C. The crude product which remains as residue is isolated by distillation in vacuo over a bridge-shaped stillhead which has been heated to 80° C.

216 g of 4-methyl-5-propoxy-2,4-dihydro-3H-1,2,4-triazol-3-one (90.35% pure, yield: 90% of theory) are obtained, and this can be obtained in pure form by recrystallization from toluene/cyclohexane (1:1). Melting point: 74° C.

EXAMPLE 12

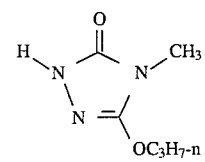

309 g (1.5 mol) of bis-(2-ethoxyethyl) carbonate are mixed with 78.75 g (1.575 mol) of hydrazine hydrate while cooling with a water-bath and the mixture is stirred for 16 hours at room temperature. After a further hour at 50° C., water of hydration, excess hydrazine and some of the ethoxyethanol formed are stripped off at 15 mbar (91 g altogether).

The residue obtained is 2-ethoxyethyl carbazinate of the formula $H_5C_2O-CH_2CH_2-O-CO-NH-NH_2$. While cooling with cold water, 238.5 g (1.5 mol) of dipropyl methylimino-carbonate and a catalytic amount (1.5 g) of pivalic acid are stirred into this residue; after 2 hours, more pivalic acid (again 1.5 g) is added. After 12 hours at room temperature, the mixture is stirred for 1 hour at 70° C., 58.4 g of a 30% solution of sodium methanolate in methanol (0.325 mol of NaOCH₃) are then added, and the mixture is stirred for 7 hours at 70° C.

The mixture is subsequently neutralized by adding 32 g of concentrated hydrochloric acid (37% strength) with ice-cooling (pH check). After all volatile components have been distilled off up to 130° C./15 mbar, the desired product is removed from the residue by distillation under a further reduced pressure (by means of oil pump) and thus separated off from the sodium chloride formed.

221 g of distillate with a 4-methyl-5-propoxy-2,4-dihydro-3H-1,2,4-triazol-3-one content of 95.8 % are obtained. Taking into consideration the samples required for analysis, this corresponds to a yield of 93% of theory.

EXAMPLE 13

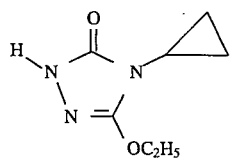

Analogously to Example 2, by reacting equimolar amounts of ethyl carbazinate and diethyl cyclopropyliminocarbonate in the presence of pivalic acid (2 mol-%) and further reacting the intermediate thereby formed with an equimolar amount of sodium methanolate there is obtained 4-cyclopropyl-5-ethoxy-2,4-dihydro-3H-1,2,4-triazol-3-one (yield: 79% of theory) of m.p. 144°–145° C. (recrystallized from water).

EXAMPLE 14

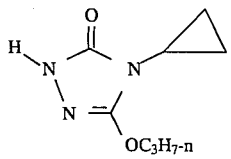

Analogously to Examples 2 and 13, but employing 2-ethoxyethyl carbazinate instead of ethyl carbazinate, there is obtained 4-cyclopropyl-5-propoxy-2,4-dihydro-3H-1,2,4-triazol-3-one (yield: 72% of theory) of m.p. 105°–106° C. (recrystallized from water).

EXAMPLE 15

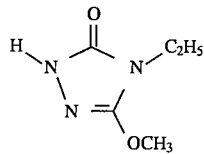

Analogously to Examples 2 and 14, there is obtained 4-ethyl-5-methoxy-2,4-dihydro-3H-1,2,4-triazol-3-one (yield: 81% of theory) of m.p. 130° C. (recrystallized from acetone).

Intermediates of the Formula (IV)

EXAMPLE (IV-1)

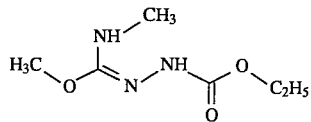

52 g (0.50 mol) of ethyl carbazinate are introduced into 400 ml of methanol, and, after 56.6 g (0.50 mol) of dimethyl methyliminocarbonate (95% pure) have been added dropwise, the mixture is stirred for 16 hours at 50° C. and, after a further 8.2 g (0.08 mol) of dimethyl methyliminocarbonate have been added, for a further hours at 50° C. It is then concentrated under a water pump vacuum, the residue is stirred with diethyl ether, and the crystalline product is isolated by filtration with suction.

75 g (86% of theory) of ethyl N'-(α-methylamino-α-methoxy-methylene)-hydrazine-N-carboxylate of melting point 128° C. are obtained.

EXAMPLE (IV-2)

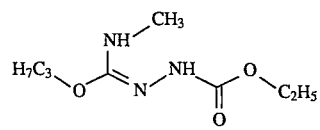

15.6 g (0.15 mol) of ethyl carbazinate are introduced into 100 ml of n-propanol, and, after 25.25 g (0.16 mol) of dipropyl methyliminocarbonate have been added dropwise, the mixture is stirred for 16 hours at 55° C. to 60° C. and, after a further 4.7 g (0.03 mol) of dimethyl methyliminocarbonate have been added, for a further hours at approximately 55° C. It is then concentrated under a water pump vacuum, the residue is stirred with methyl t-butyl ether, and the crystalline product is isolated by filtration with suction.

24.65 g (81% of theory) of ethyl N'-(α-methylamino-α-propoxy-methylene)-hydrazine-N-carboxylate of melting point 104° C. are obtained.

We claim:

1. A process for the preparation of an alkoxytriazolinone of the formula

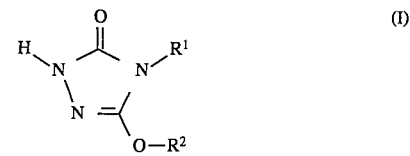

(I)

in which

R$^1$ represents alkyl, alkenyl or alkinyl, each of which has up to 6 carbon atoms and each of which is optionally substituted by halogen or C$_1$–C$_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or C$_1$–C$_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, C$_1$–C$_4$- alkyl, C$_1$–C$_4$-halogenoalkyl, C$_1$–C$_4$-alkoxy, C$_1$–C$_4$-halogenoalkoxy or C$_1$–C$_4$-alkoxy- carbonyl, and R$^2$ represents alkyl, alkenyl or alkinyl, each of which has up to 6 carbon atoms and each of which is optionally substituted by halogen or C$_1$–C$_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or C$_1$–C$_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, C$_1$–C$_4$-alkyl, C$_1$–C$_4$, halogenoalkyl, $C_1$–$C_4$-alkoxy, $C_1$–$C_4$-halogenoalkoxy or $C_1$–$C_4$-alkoxy-carbonyl, which comprises in a first step reacting an iminocarbonic diester of the formula

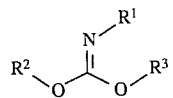
(II)

in which $R^3$ represents in each case optionally substituted $C_1$–$C_4$-alkyl, phenyl or benzyl wherein the substituents are $C_1$–$C_4$-alkoxy, phenoxy or benzyloxy, with a carbazinic ester of the formula

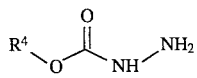
(III)

in which $R^4$ represents optionally substituted $C_1$–$C_4$-alkyl, phenyl or benzyl wherein the substituents are $C_1$–$C_4$-alkoxy, phenoxy or benzyloxy, optionally in the presence of a reaction auxiliary and optionally in the presence of a diluent at a temperature between $-20°$ C. and $+120°$ C. wherein the reaction auxiliary is a protonic acid, a polymeric acid or an acidic ion exchanger thereby to form a semicarbazide derivative of the formula

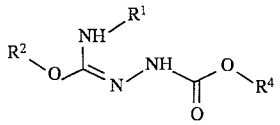
(IV)

and in a second step subjecting the compound of the formula (IV) to a cyclizing condensation reaction at a temperature between $20°$ C. and $100°$ C., optionally after intermediate isolation, in the presence of a base and optionally in the presence of a diluent.

2. A process according to claim 1, wherein the first step is effected at from $0°$ to $100°$ C.

3. A process according to claim 1, wherein the first step is effected at from $20°$ to $80°$ C.

4. A process according to claim 1, wherein the second step is effected at $30°$ to $90°$ C.

5. A process according to claim 1, wherein the second step is effected at $40°$ to $80°$ C.

6. A process according to claim 1, wherein II is dimethyl methyliminocarbonate, diethyl methyliminocarbonate, dipropyl methyliminocarbonate or O-(2-ethoxyethyl)-O-n-propyl methyliminocarbonate.

7. A process according to claim 1, wherein III is ethyl carbazinate.

8. A process according to claim 1, wherein each of the first and second steps is effected in the presence of a diluent.

9. A process according to claim 8, wherein the diluent is methanol, ethanol, n-propanol or i-propanol.

10. A process according to claim 1, wherein the first step is effected in the presence of a protonic acid as a reaction auxiliary.

11. A process according to claim 10, wherein the protonic acid is pivalic acid, acetic acid or optionally aqueous hydrochloric acid.

12. A process according to claim 1, wherein the base employed in the second step is an alkali metal alcoholate or alkali metal hydroxide.

13. A process according to claim 1, in which $R^3$ is methyl, ethyl, propyl, cyclo-propyl, methoxyethyl or ethoxyethyl, and $R^4$ is methyl, ethyl, propyl, methoxyethyl or ethoxyethyl.

* * * * *